(12) United States Patent
Dong et al.

(10) Patent No.: US 6,768,122 B2
(45) Date of Patent: Jul. 27, 2004

(54) MULTIPHOTON EXCITATION MICROSCOPE FOR BIOCHIP FLUORESCENCE ASSAY

(75) Inventors: Chen-Yuan Dong, Taipei (TW); Peter T. C. So, Cambridge, MA (US); Sunney I. Chan, Taipei (TW)

(73) Assignee: National Taiwan University, Taipei (TW)

(*) Notice: Subject to any disclaimer, the term of this patent is extended or adjusted under 35 U.S.C. 154(b) by 105 days.

(21) Appl. No.: 10/160,251

(22) Filed: Jun. 4, 2002

(65) Prior Publication Data

US 2003/0222222 A1 Dec. 4, 2003

(51) Int. Cl.[7] .............................................. G01N 21/64
(52) U.S. Cl. ................................................. 250/458.1
(58) Field of Search ...................................... 250/458.1

(56) References Cited

U.S. PATENT DOCUMENTS 5,815,262 A * 9/1998 Schrof et al. ............ 250/458.1
6,461,492 B1 * 10/2002 Hayashizaki et al. ....... 204/603
6,603,537 B1 * 8/2003 Dietz et al. .............. 250/458.1
6,603,546 B1 * 8/2003 Barbieri et al. .......... 250/458.1
6,630,680 B2 * 10/2003 Hakamata et al. ....... 250/458.1
2002/0036775 A1 * 3/2002 Wolleschensky et al. ... 356/317
2002/0109100 A1 * 8/2002 Jackson et al. .......... 250/458.1

* cited by examiner

Primary Examiner—Constantine Hannaher
(74) Attorney, Agent, or Firm—Dennison, Schultz, Dougherty & Macdonald

(57) ABSTRACT

A multiphoton excitaion microscope for simultaneously detecting differently colored fluorescence materials on biochips includes a multiphoton excitation source, objectives, and a plurality of detection channels. The biochip is hybridized and labeled with fluorescence materials for expressing hybridized biological signals. The multiphoton excitation source is focused to a light spot on the biochip to excite the fluorescence materials bound thereon. After that, the fluorescence emission at different wavelengths from the different fluorescent materials can be detected by the plural detection channels.

16 Claims, 2 Drawing Sheets

MULTIPHOTON EXCITATION MICROSCOPE FOR BIOCHIP FLUORESCENCE ASSAY

FIELD OF THE INVENTION

The present invention relates to a fluorescence analytical apparatus for biochips fluorescence assay, and more specifically, a multiphoton excitation microscope which is applied to simultaneously excite several different fluorescence materials for effectively increasing the analytical efficiency.

BACKGROUND OF THE INVENTION

With the sequencing of human gene maps now on the verge of completion, the next challenge facing scientists is to understand the meanings and relationships among the thousands of genes, and to research the functions of proteins. Biochip technology is a power methodology to address this problem by its ability to monitor protein expression efficiently. The main characteristics of the biochip technology are providing accurate and rapid analysis, using less samples and reagents than conventional biochemical techniques, and monitoring the protein expression profiles of multiple proteins from different samples in a single experiment simultaneously. Due to the above characteristics, the biochip technology has found wide applications in gene function research, new drug development, disease detection, and clone selection. Undoubtedly, biochip technology will be a key biotechnological research tool in the 21st century.

The biochip is a micro instrument. Scientists use extremely accurate technology to sequentially spot minute quantities of specific biological materials on a tiny carrier, manufactured from paper, glass, silicon, or other materials, for performing various examinations of biological samples.

Biochips are classified into DNA chips (also called gene chips), protein chips, and microfluidic chips, with the DNA chip being the most developed technology. The principle on which the DNA chip is based is the fabrication of a high density array of thousands of single stranded DNAs (also called probes) localized on biological materials (generally called "chips") manufactured from glass, nylon, or other materials. Two main sources of single stranded DNAs exist, oligonucleotide and complementary DNA (cDNA). The oligonucleotide chip is mainly manufactured by Affymetrix co., using A' T' C' G bases, which comprise DNA, to construct 20 to 25 bases of the oligonucleotide. The cDNA chip uses the extract known as cDNA, taken from patient samples or other organisms. Then different oligonucleotide or cDNA sequences are positioned onto the chip in an orderly array.

To perform the gene expression analysis, the messenger RNA of the sample is extracted and reversely transcribed to cDNA. The cDNA sequences obtained are then labeled with fluorescent materials and hybridized with the probes on the chip. The fluorescent signals are received and recorded using fluorescence imaging techniques such as confocal microscope. From analyzing the fluorescence pattern, gene expression patterns of the samples can be monitored.

One of the most widely applications of the biochip technology is the study of diseases. Since over 60% of diseases are related to gene defects or abnormalities, knowledge of gene expression and functions is helpful in comprehending the mechanism of a disease, and can lead to the development of preventive and therapeutic measures. Therefore, researchers use a complex procedure to obtain proteins or genes samples through blood drawing, separation, braking, extraction, selection and signal amplifying hoping to identify gene-based diseases. These genes or proteins are subsequently used as biological materials for fabrication onto the biochips which then act as tamplates in examinations and experiments. The hybridization of the reversely transcribed and fluorescently tagged cDNA's with the biochip is monitored by fluorescence imaging techniques. A commonly used imaging technique is confocal microscopy. In most confocal microscopes, single-photon excitation is used to excite the fluorescent molecules. While single-photon confocal microscopy has been successfully applied to biochip fluorescence assay, this technique also has its limitation. Specifically, the light source of the confocal microscope is only capable of exciting fluorescent molecules whose wavelength is spectrally closed to the fluorescent emission. As a result, fluorescence analysis using single-photon excitation in multi-colored biochip analysis is difficult to achieve because a single-photon exciting wavelength cannot simultaneously excite fluorescent species with different emission characteristics. As a result, biochip analysis of multiple samples cannot be easily achieved using confocal microscope.

SUMMARY OF THE INVENTION

The first purpose of this invention is providing a multiphoton excitation microscope for detecting the fluorescence materials on a biochip.

The second purpose of this invention is providing a multiphoton excitation microscope for simultaneously detecting differently colored fluorescence materials on the biochip.

The third purpose of this invention is providing a multiphoton excitation microscope with multiple detection channels to increase the speed and efficiency of performing biochip fluorescence assay.

This invention provides a multiphoton excitation microscope to simultaneously excite differently colored fluorescence materials of the biochip for effectively increasing the analytical efficiency. The microscope includes a gene chip, a multiphoton excitation light source such as the titanium-sapphire laser system, a beam scanner, an objective, and a plurality of detection channels. The gene chip is fabricated with high density of thousands of single stranded DNA. After hybridizing the single stranded DNA probes with fluorescently tagged cDNA's from the samples, the hybridization can be monitored using the multiphoton fluorescence imaging technique. Output of the titanium-sapphire laser system is passed through the beam scanner, and focused to a light spot by the objective to scan and excite the fluorescent materials hybridized onto the gene chip. Finally, the spectrally specific fluorescence is collected by the microscope objective and simultaneously recorded using the multiple detection channels.

BRIEF DESCRIPTION OF THE DRAWINGS

The foregoing, and additional objectives, features and advantages of the present invention will become apparent following the description of preferred embodiments thereof, taken in conjunction with the accompanying drawings, in which.

DETAILED DESCRIPTION OF THE PREFERRED EMBODIMENT

In order to solve all the disadvantages taken from single-photon excitation, this invention discloses a multiphoton excitation microscope applied to substitute the traditional single-photon confocal microscope for obviously increasing the efficiency of analyzing the biochip. The two-photon excitation is illustrated below to excite the fluorescence.

Two-photon excitation refers to the simultaneous absorption of two photons with the frequencies v1 and v2 by the fluorescent molecule. Energetically, this process if equivalent to the molecular excitation by a photon with a frequency equal to the sum of v1 and v2. Because two photons are involved in two-photon excitation, the transition rate increases with the square of the incident photon flux. In addition, since the two-photon absorption cross-section is low, high instantaneous power is needed to ensure efficient excitation.

Figure 1:
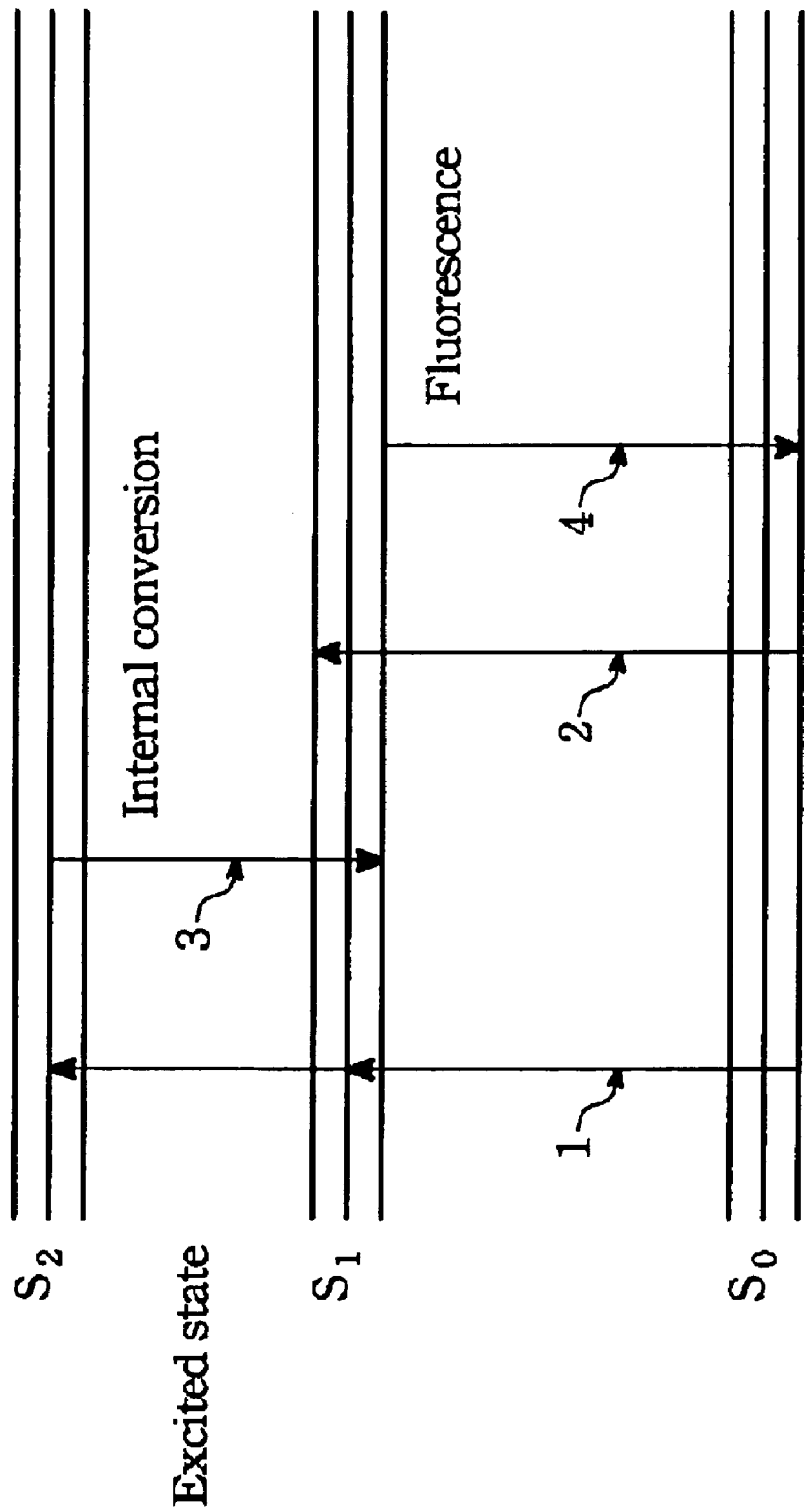
FIG. 1 is the Jablonski diagram illustrating the typical energy converting during the fluorescence generation.

The emitting fluorescence originats from the electron transition of an atom or a molecule. FIG. 1 illustrates the Jablonski diagram used to demonstrate the energy level transition resulting in fluorescence generation. In this diagram, S0 represents the ground singlet state, and the S1 and S2 represent the first and the second excited singlet states of electrons, respectively. In the case that no photon is absorbed, the Boltzmann distribution measuring the relative population of the excited to the ground state molecules can be expressed as the following:

$$R = e^{-\Delta E/KT}$$

where $\Delta E$ indicates the energy gap between band levels, K represents the Boltzmann constant, and T is the absolute temperature. At room temperature, most molecules are at the ground state. As a result, little fluorescence emission is observed. However, when a photon with specific wavelength is absorbed by object molecules, the molecules are excited to higher energy levels represented by S1 (arrow 2) and S2 (arrow 1). Generally speaking, the molecules at the S2 energy level will quickly decay to the S1 (arrow 3) energy level by non-radiative transition. Subsequently, the molecules at the S1 energy level decay to the S0 (arrow 4) energy level and produce fluorescence in the process. Typically, fluorescence emission occurs on the time scale of around 10 nanoseconds. Notedly, the excited fluorescence can also be taken from two-photon or multiphoton excitation.

Figure 2:
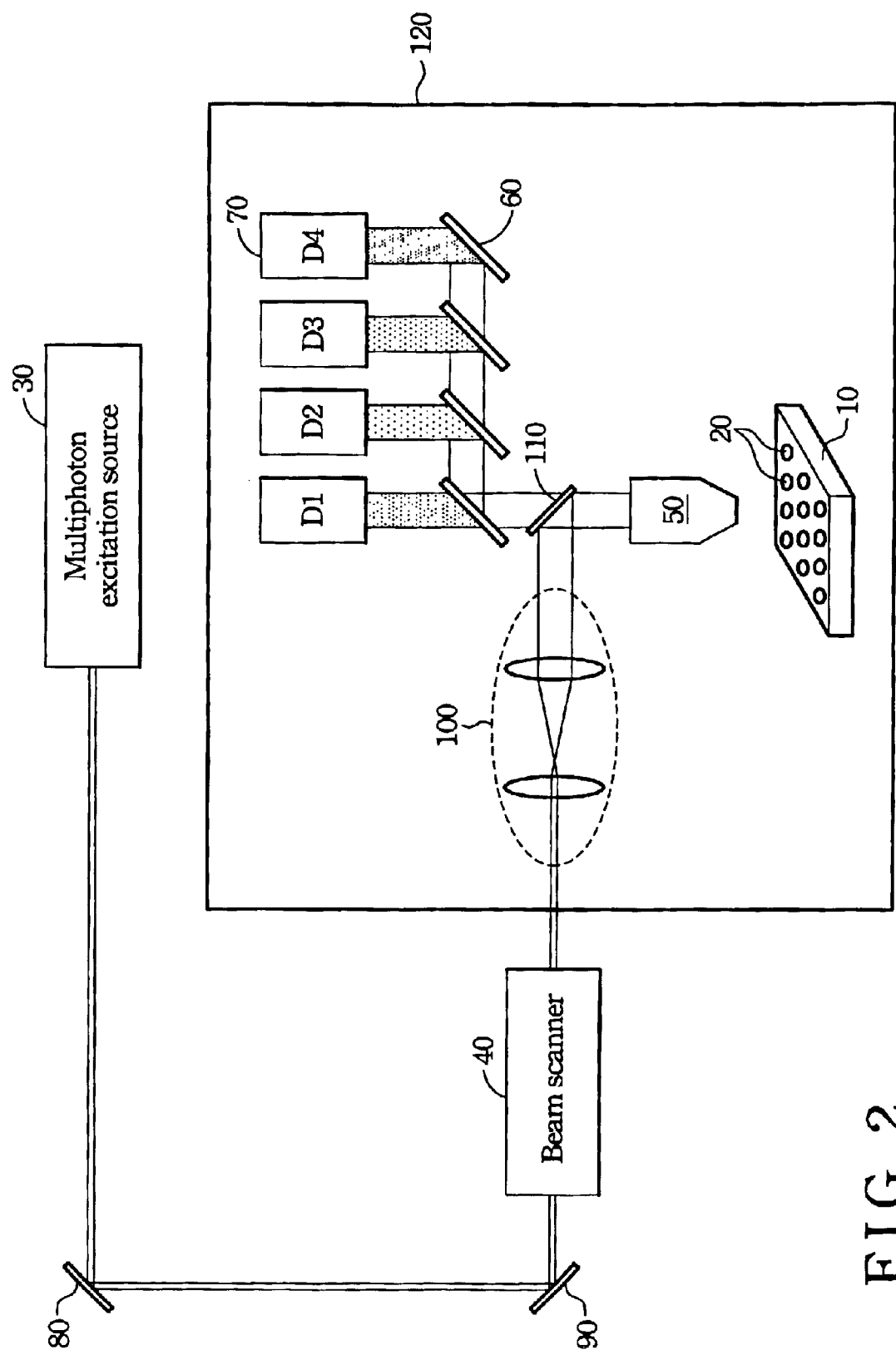
FIG. 2 is a diagrammatic illustrating a multiphoton excitation microscope described in accordance with the present invention.

FIG. 2 discloses a multiphoton excitation microscope 120 for simultaneously exciting differently colored fluorescence materials on a biochip to effectively increase the analysis efficiency.

First the biochip 10 is spotted high density of thousands of single stranded DNAs 20 (also called probes). The material of the biochip can be chosen from glass, nylon, or other materials. The source of the single stranded DNAs can be chosen from oligonucleotides or complementary DNAs (cDNAs). The single stranded DNAs can also be selected from proteins, antigens, or antibodies based on the experiments needs. Next, the messenger RNAs of samples are extracted, and reversely transcribed to cDNAs. The cDNAs are labeled with fluorescence materials prior to biochip 10 hybridization with the probes 20 (single stranded DNAs).

After hybridizing of the probes 20 with the labeled cDNAs, the biochip 10 has bound fluorescence. The fluorescence is the hybridized biological signals, and is examined by a multiphoton excitation microscope. A multiphoton excitation source 30 of the multiphoton excitation microscope can generate exciting light for simultaneously exciting differently colored fluorescence materials on the biochip 10. In one preferred embodiment, titanium-sapphire laser system is chosen to excite the near-infrared light whose wavelength is between 700 nm to 1000 nm.

When the exciting light is emitted from the multiphoton excitation source 30, it is reflected in sequence by the first mirror 80 and the source 30, it is reflected in sequence by the first mirror 80 and the second mirror 90 and is transmitted to a beam scanner 40. Then the light delivered from the beam scanner is amplified and paralleled by a beam mirror means 100. Subsequently the light beam is focused to a light spot by an objective 50 to excite the fluorescence bound on the biochip 10.

Note that the fluorescence (the hybridized biological signals) of the biochip 10 can be scanned one by one with this light beam according to the beam scanner setting. Then the excited fluorescence having characteristic wavelengths is received by the objective 50. After that, the fluorescence is separated by a dichroic mirror 110 into the different detection channels. The passed fluorescence can be filtered individually by using multiple filters 60, following detecting the fluorescence by the respective detection channels 70. In the preferred embodiment, four sets of filters and detection channels are applied to detect the fluorescence, and the filters can also be chosen from prisms or gratings. At last, the biological signals carried by the fluorescence are transmitted to a computer for data analysis.

There are a number of advantages in examining the biological signals on the biochip using multiphoton excitation microscope:

(1) Because the differences of the excited wavelengths between multiphoton and emitting fluorescence are considerable large, the intact emitting spectrum can be easily obtained.

(2) In addition, the differently colored fluorescence materials can be excited simultaneously by the multiphoton excitation microscope, so multi-color fluorescence analysis of the biochip can be examined simultaneously. These make the applications of the multiphoton excitation microscope more variable, increase the analytical efficiency and decrease the biochip consumption to prevent the high cost;

(3) To confine specimen photodamage to the vicinity of the focal "point."

While the preferred embodiment of the invention has been illustrated and described, it will be appreciated that various changes can be made therein without departing from the spirit and scope of the invention.

What is claimed:

1. A multiphoton excitation microscope for investigating expression of optical signals on a biochip wherein an array of probes fabricated on said biochip is hybridized with sample extractions labeled with fluorescence, which comprises:

a multiphoton excitation source to excite a light beam;

a beam scanner receiving the light beam transmitted from said multiphoton excitation source;

a dichroic mirror reflecting the light beam from said scanner;

an objective focusing the light beam to a light spot for exciting said optical signals;

said dichroic mirror separating the fluorescent light from said optical signals;

a plurality of filters for filtering respective wavelengths of fluorescence of the fluorescent light; and a plurality of detection channels for detecting respective fluorescence simultaneously.

2. The microscope of claim 1, wherein said multiphoton excitation source is a titanium-sapphire laser system whose near-infrared output is between 700 nm to 1000 nm in wavelength.

3. The microscope of claim 1, wherein said filters comprises prisms, gratings or the combination thereof.

4. The microscope of claim 1, wherein said probes comprise single stranded DNAs, proteins, antigens, antibodies or any combination thereof.

5. The microscope of claim 4, wherein said probes comprise oligonucleotide, complementary DNAs or any combination thereof.

6. A multiphoton excitation microscope for investigating expression of optical signals on a biochip wherein an array of probes fabricated on said biochip is hybridized with sample extractions labeled with fluorescence, which comprises:

a multiphoton excitation source to excite a light beam;

a beam scanner receiving the light beam transmitted from said multiphoton excitation source;

a beam mirror means for amplifying and paralleling the light beam from said beam scanner;

a dichroic mirror reflecting the light beam from said beam mirror means;

an objective focusing the light beam to a light snot for exciting said optical signals;

said dichroic mirror separating the fluorescent light from said optical signals;

a plurality of filters for filtering respective wavelengths of fluorescence of the fluorescent light; and a plurality of detection channels for detecting respective fluorescence simultaneously.

7. The microscope of claim 6, wherein said multiphoton excitation source is a titanium-sapphire laser system whose near infrared output is between 700 nm to 1000 nm in wavelength.

8. The microscope of claim 6, wherein said filters comprises prisms, gratings or the combination thereof.

9. The microscope of claim 6, wherein the number of said detection channels is four.

10. The microscope of claim 6, wherein said probes comprise single stranded DNAs, proteins, antigens, antibodies or the combination thereof.

11. The microscope of claim 10, wherein probes comprise oligonucleotide, complementary DNAs or the combination thereof.

12. A multiphoton excitation microscope for investigating expression of optical signals on a gene chip wherein an array of probes fabricated on said gene chip is hybridized with sample extractions labeled with fluorescence, which comprises:

a titanium sapphire laser system to excite a light beam;

a beam scanner receiving said light beam transmitted from said titanium sapphire laser system;

a beam mirror means for amplifying and paralleling said light beam from said beam scanner;

a dichroic mirror reflecting said light beam from said beam minor means;

an objective focusing said light beam to a light spot for exciting said optical signals;

said dichroic mirror separating the fluorescent light from said optical signals;

a plurality of filters for filtering respective wavelengths of fluorescence of the fluorescent light; and a plurality of detection channels for detecting respective fluorescence simultaneously;

a plurality of detection channels for detecting respective fluorescence simultaneously.

13. The microscope of claim 12, wherein said titanium-sapphire laser system generates the near-infrared light whose wavelength is between 700 nm to 1000 nm.

14. The microscope of claim 12, wherein said filters comprises prisms, gratings or the combination thereof.

15. The microscope of claim 12, wherein the number of said detection channels is four.

16. The microscope of claim 12, wherein probes comprise oligonucleotide, complementary DNAs or the combination thereof.

* * * * *